United States Patent
Daniel

(10) Patent No.: US 9,616,160 B2
(45) Date of Patent: Apr. 11, 2017

(54) BLOOD TREATING DEVICE

(75) Inventor: Pia Daniel, Bodman (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1798 days.

(21) Appl. No.: 10/557,823

(22) PCT Filed: May 13, 2004

(86) PCT No.: PCT/EP2004/005115
§ 371 (c)(1),
(2), (4) Date: Feb. 13, 2007

(87) PCT Pub. No.: WO2004/103442
PCT Pub. Date: Dec. 2, 2004

(65) Prior Publication Data
US 2007/0235376 A1    Oct. 11, 2007

(30) Foreign Application Priority Data

May 23, 2003    (DE) .................................. 103 23 843

(51) Int. Cl.
*B01D 61/28* (2006.01)
*A61M 1/16* (2006.01)

(52) U.S. Cl.
CPC ......... *A61M 1/16* (2013.01); *A61M 2205/505* (2013.01)

(58) Field of Classification Search
CPC ..................... A61M 1/16; A61M 2205/505
USPC .... 210/85, 138, 645, 646; 604/5, 35; 700/83
See application file for complete search history.

(56) References Cited

U.S. PATENT DOCUMENTS

| 4,267,040 | A |   | 5/1981 | Schäl |
| 5,247,434 | A | * | 9/1993 | Peterson et al. ................. 700/83 |
| 5,609,770 | A | * | 3/1997 | Zimmerman et al. ......... 210/739 |
| 5,707,086 | A | * | 1/1998 | Treu et al. ....................... 285/93 |
| 5,858,239 | A |   | 1/1999 | Kenley et al. |
| 6,738,052 | B1 |  | 5/2004 | Manke et al. |
| 7,108,672 | B2 |  | 9/2006 | Steele et al. |

(Continued)

FOREIGN PATENT DOCUMENTS

| EP | 0 623 357 A1 | 11/1994 |
| EP | 0 904 788 A1 | 3/1999 |

(Continued)

*Primary Examiner* — Dirk Bass
(74) *Attorney, Agent, or Firm* — Jacobson Holman, PLLC.

(57) ABSTRACT

A blood treatment unit has a blood treatment device which is part of an extracorporeal blood circulatory system. The unit has a control unit and a display and input unit having a touch screen. In order to simplify the operation of the blood treatment unit using the touch screen, the control unit and the display and input unit are suitable for representing various mode means on the touch screen which correspond to the various time modes of the blood treatment. The control unit automatically instigates the beginning of the following time mode at the end of at least one time mode, this being indicated by a change in the representation of the selected mode means on the touch screen. It is especially advantageous to use sensors through whose measured values the control unit identifies the end of one time mode and the beginning of the subsequent time mode.

17 Claims, 6 Drawing Sheets

(56) References Cited

U.S. PATENT DOCUMENTS

2002/0085952 A1 7/2002 Ellingboe et al.
2003/0135152 A1* 7/2003 Kollar et al. .................. 604/35

FOREIGN PATENT DOCUMENTS

| JP | 7-136250 | 5/1995 |
| JP | 11-504836 | 5/1999 |
| WO | WO 96/40322 | 12/1996 |
| WO | WO 02/26288 A2 | 4/2002 |

* cited by examiner

BLOOD TREATING DEVICE

CROSS-REFERENCE TO RELATED APPLICATION

This is a nationalization of PCT/EP04/005115 filed May 13, 2004 and published in German.

BACKGROUND OF THE INVENTION

1. Field of Invention

The invention relates to blood treatment equipment comprising a blood treatment device which is part of an extracorporeal blood circulatory system. The equipment includes actuators, a control unit for controlling the actuators, and a display and input unit including a touch screen connected to the control unit.

2. Description of the Prior Art

Various devices are known for the extracorporeal treatment of blood. In these devices blood is passed via a blood supply line from a patient to a blood treatment device and from there is passed back to the patient via a blood return line. The blood treatment device can, for example, be a haemodialyser or haemofilter, a blood oxygenator, a blood adsorber or a blood centrifuge. Such devices comprise actuators for controlling the blood treatment which are controlled by a control unit of the blood treatment equipment for the specific sequence of the blood treatment.

As a result of the numerous possible uses of this equipment and necessary safety measures, this equipment is relatively complex. For the operator there is increasingly the risk of the display and input interface being unclear. In view of the availability of new media, touch screens are increasingly being used for display and input units of such equipment. Thus, EP 0 904 788 A1 discloses the use of a touch screen to facilitate the operation of the equipment with the aid of a graphical image of the components of the haemodialysis equipment.

U.S. Pat. No. 5,609,770 discloses an operator-machine interface with a touch screen for a haemodialysis device in which the focus is on the input of parameters and in which individual parameters are divided into groups. The input of parameters for a haemodialysis treatment using a touch screen is also the subject matter of EP 0 623 357 A1. The input and reproduction of specific information on an extracorporeal drip chamber in a haemodialysis treatment using a touch screen is the subject matter of U.S. Pat. No. 5,858,239.

In an extracorporeal blood treatment a plurality of temporally successive modes are passed through. Apart from the actual blood treatment mode, there is a preceding blood treatment preparation mode and a subsequent blood treatment after-preparation mode. In the blood treatment preparation mode the extracorporeal blood circulatory system is prepared for the blood treatment mode, by removing air or another medium from the extracorporeal circulatory system and introducing an isotonic filling fluid, generally sodium chloride solution, into the extracorporeal blood circulatory system. At the end of a blood treatment the blood located in the extracorporeal blood circulatory system is to be re-infused into the patient during a blood treatment after-preparation mode.

SUMMARY OF THE INVENTION

Starting from the known haemodialysis equipment, the invention has set itself the object of simplifying the operation of a blood treatment device using a touch screen taking special account of the temporally successive blood treatment modes.

According to the teaching of the invention, this object is solved by a blood treatment device having the features described herein. Various advantageous embodiments of the invention are also described herein.

BRIEF DESCRIPTION OF THE DRAWINGS

Further details and advantages of the invention are described in detail with reference to an exemplary embodiment shown in the drawings. In this embodiment the blood treatment device is a haemodialysis device. In the figures.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
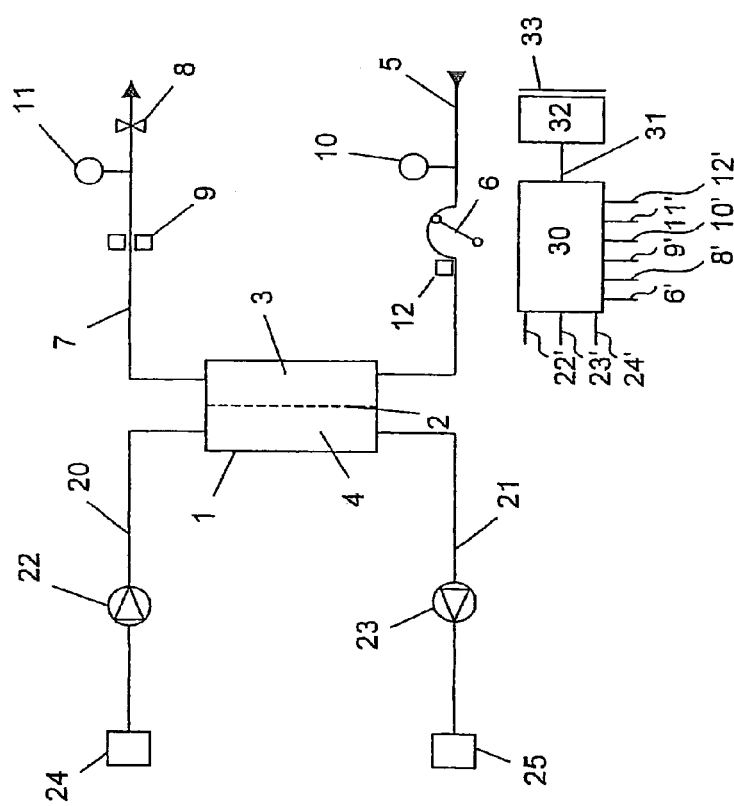
FIG. 1 is a highly schematic view of the haemodialysis device.

The structure of a haemodialysis device is first explained briefly with reference to FIG. 1. In haemodialysis, blood is supplied in an extracorporeal circulatory system via a blood supply line 5 to a blood purification element implemented as a haemodialyser 1. In the haemodialyser 1 a semi-permeable membrane 2 generally implemented in the form of many hollow fibres separates a first chamber 3, which is part of the extracorporeal blood circulatory system, from a second chamber 4 which is part of a dialysis fluid circulatory system. Substances to be removed from the blood pass through the semi-permeable membrane 2 into the dialysis fluid and are removed by said fluid. At the same time, an excess quantity of fluid can be ultrafiltered from the blood via a pressure gradient and removed by means of the outflowing dialysis fluid.

In the blood supply line 5 blood is transferred by a blood pump 6 configured as a roller pump. The blood leaves the first chamber 3 of the haemodialyser 1 via the blood return line 7 to be returned back to the patient. Provided on the blood return line 7 is a venous shut-off clamp 8 with which the return of the blood can be interrupted especially in emergencies. Such emergencies can occur, for example, if air is detected in the blood return line 7 by an air and blood detector 9. The air and blood detector 9 also comprises means for identifying the presence of blood in the blood return line 7.

An arterial pressure sensor 10 is provided on the blood supply line 5 and a venous pressure sensor 11 is provided on the blood return line 7.

Dialysis fluid flows through the second chamber 4 of the haemodialyser, which fluid is supplied via a dialysis fluid supply line 20 from a dialysis fluid source 24 and is removed via a dialysis fluid removal line 21 to an outflow 25. The dialysis fluid is circulated by conveying and balancing devices 22 and 23 wherein the quantity of any ultrafiltrate to be removed can be registered precisely.

The person skilled in the art has various arrangements at his disposal for implementing the conveying and balancing devices 22 and 23 so that further details are not given at this point. The same applies to the provision of dialysis fluid by the dialysis fluid source 24. As an example, reference is made to a balance chamber system such as that described in U.S. Pat. No. 4,267,040.

Numerous possibilities for the use of actuators and sensors in a haemodialysis device are also generally available to the person skilled in the art without it being necessary to go into detail here. The diagram in FIG. 1 is restricted to a few of these elements which are sufficient for explaining the invention.

The haemodialysis device is controlled and monitored by a control unit 30. For this purpose the control unit 30 is connected to the individual actuators and sensors of the equipment using signal leads. For the actuators and sensors shown in FIG. 1 this is indicated by reference numbers which have an apostrophe next to the reference number of the relevant actuator or sensor and which for the sake of clarity are only indicated at the control unit 30.

The control unit 30 is connected to an output and input unit 32 via a data link 31. The output and input unit 32 comprises a touch screen 33. Information notified by the control unit 30 is displayed on the touch screen and at the same time, data entered by an operator via the touch screen is passed on to the control unit 30.

Figure 2:
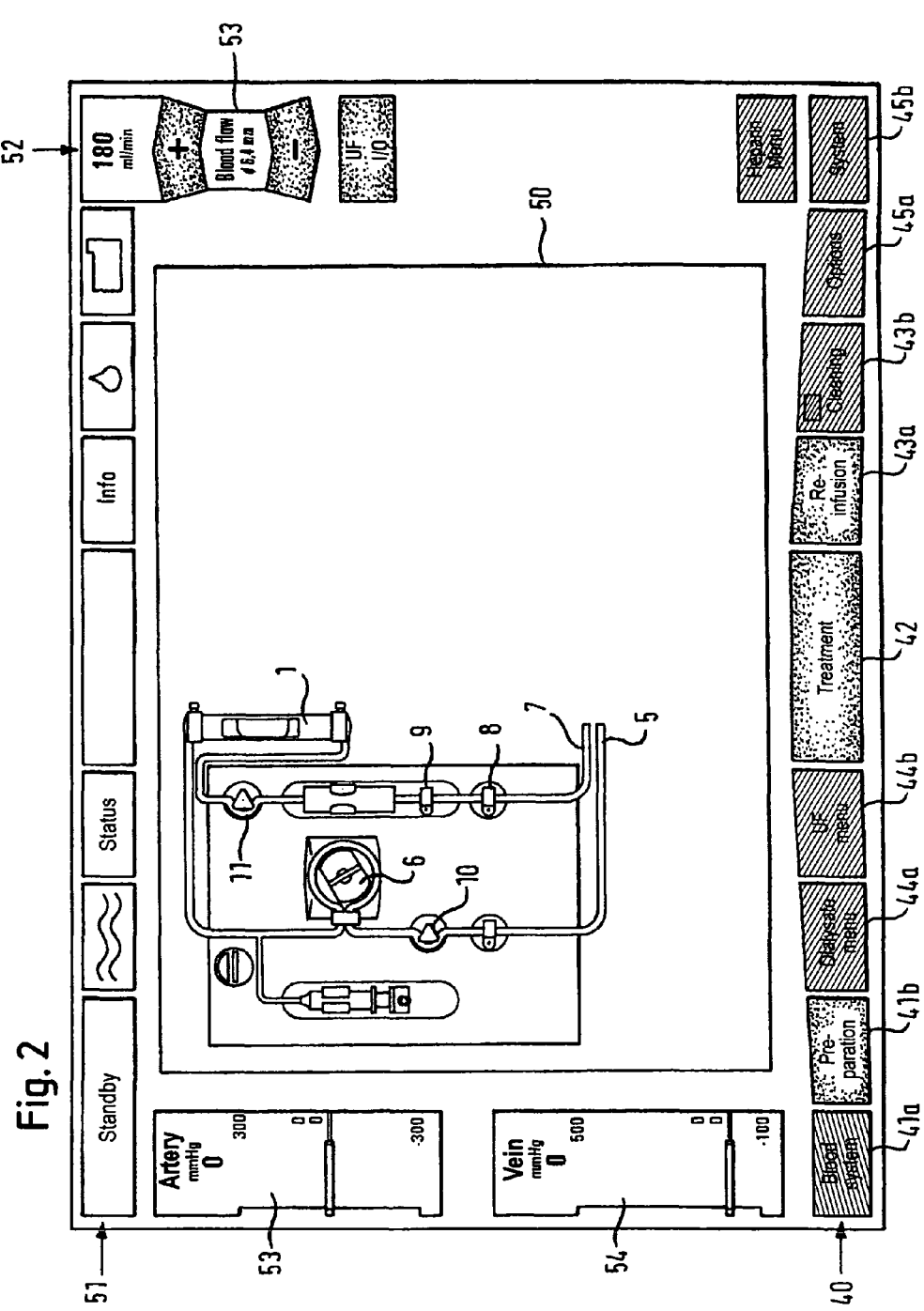
FIG. 2 is a first view of a touch screen of the haemodialysis device with various mode means, wherein the mode means "blood system" is selected.

FIG. 2 shows a first view of the touch screen 33 of the haemodialysis device. At the lower edge of the touch screen are various mode means 40 in an adjacent row. The mode means 40 comprise various types of mode means.

Firstly there are blood treatment preparation means 41a and 41b, blood treatment means 42 and blood treatment after-preparation means 43a and 43b, i.e., these mode means relate to time modes before a blood treatment—a haemodialysis treatment in this case—, the actual blood treatment and after a blood treatment. In each of these modes the haemodialysis device runs through specific process steps, with the modes proceeding in a certain time sequence.

Furthermore, supplementary mode means 44a, 44b and 45a and 45b are provided to make it possible to enter supplementary information at a plurality of time points. The meaning of the individual modes is described in detail in the continuation of the description.

Arranged on the touch screen 33 above the mode means 40 is a display area 50 on which various views are to be seen according to the operating mode. In the edge regions 51, 52 further input and/or output means (for example, means 53 for the blood pump 6) are provided to make it possible to make specific data inputs and display desired information.

These edge regions can have the same structure regardless of the operating mode or they can depend thereon. Since this part of the touch screen is of secondary importance for the explanation of the invention, this is not discussed in further detail at this point.

At the beginning of the haemodialysis treatment the haemodialysis device switches into the "blood system" mode (FIG. 2). If the device does not identify an inserted blood hose by means of a suitable sensor, e.g. a mechanical contact sensor 12 on the blood pump 6, this mode is automatically displayed by the control unit 30. Otherwise it is skipped and the control unit 30 triggers the selection of the temporally successive preparation mode.

In the blood system mode a graphical image of a blood hose system mounted on the haemodialysis device is shown on the display area 50 to facilitate the insertion of a blood hose system for the user. In this case, the haemodialyser 1, the blood supply line 5, the blood pump 6, the arterial pressure sensor 10, the blood return line 7, the venous clamp 8, the air and blood detector 9 and the venous pressure sensor 11 can be identified in accordance with FIG. 1.

The display and input unit 32 can represent the mode means 40 on the touch screen 33 by three types of symbols.

Firstly, those mode means which can be selected manually via the touch screen 33 in the instantaneous mode are represented in a first type of symbol. For the view shown in FIG. 2 this relates to the mode means 44a, 44b, 43b and 45. The mode means which displays the currently selected mode (blood system mode means 41a in FIG. 2) is displayed in a second type of symbol. A third type of symbol is used for the remaining mode means which are deactivated in the current mode. In FIG. 2 these are the mode means 41b, 42 and 43a.

On the left side of the view of the touch screen the measured values of the arterial and venous pressure sensors 10 and 11 are displayed in the form of bar displays 52 and 53.

After the control unit 30 has detected the presence of a correctly inserted hose system using the sensor 12, according to the invention it triggers the end of the blood system mode and the beginning of the temporally following preparation mode. The display and input unit 32 is in this case instructed to represent the mode means 40 accordingly.

Figure 3:
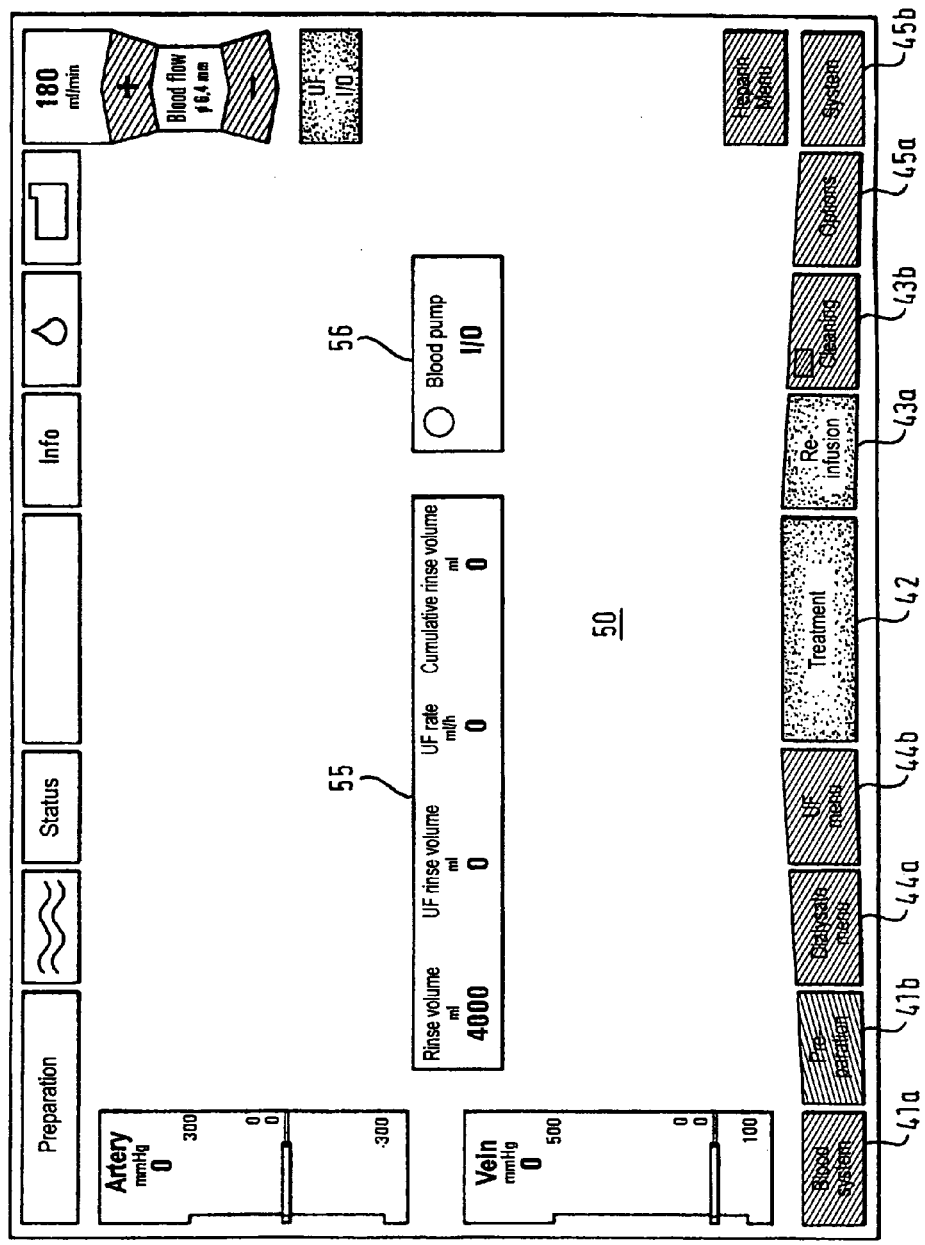
FIG. 3 is a second view of the touch screen of the haemodialysis device with various mode means, wherein the mode means "preparation" is selected.

The mode means 41b is now selected automatically and the view changed to that shown in FIG. 3.

The view in display area 50 of the touch screen 33 now shows in the data strip 55 a view of parameters such as are representative for the progress of the flushing of the blood hose system. During the flushing, for example, a bag containing physiological saline solution is connected to the blood supply line 5. The blood return line 7 leads to an outflow. At least 4 liters of sodium chloride solution are available for satisfactory flushing. By actuating the blood pump activating means 56 the blood pump is switched on with a previously set delivery flow. The data in the data strip 55 then show the respective current values. If a sufficient quantity of flushing fluid has been conveyed by the extracorporeal circulatory system, the blood pump 6 is automatically stopped by the control unit 30 on reaching the pre-determined flushing target volume. It is also possible to end the flushing manually by the blood pump activating means 56 should a smaller flushing volume be considered as sufficient.

Figure 4:
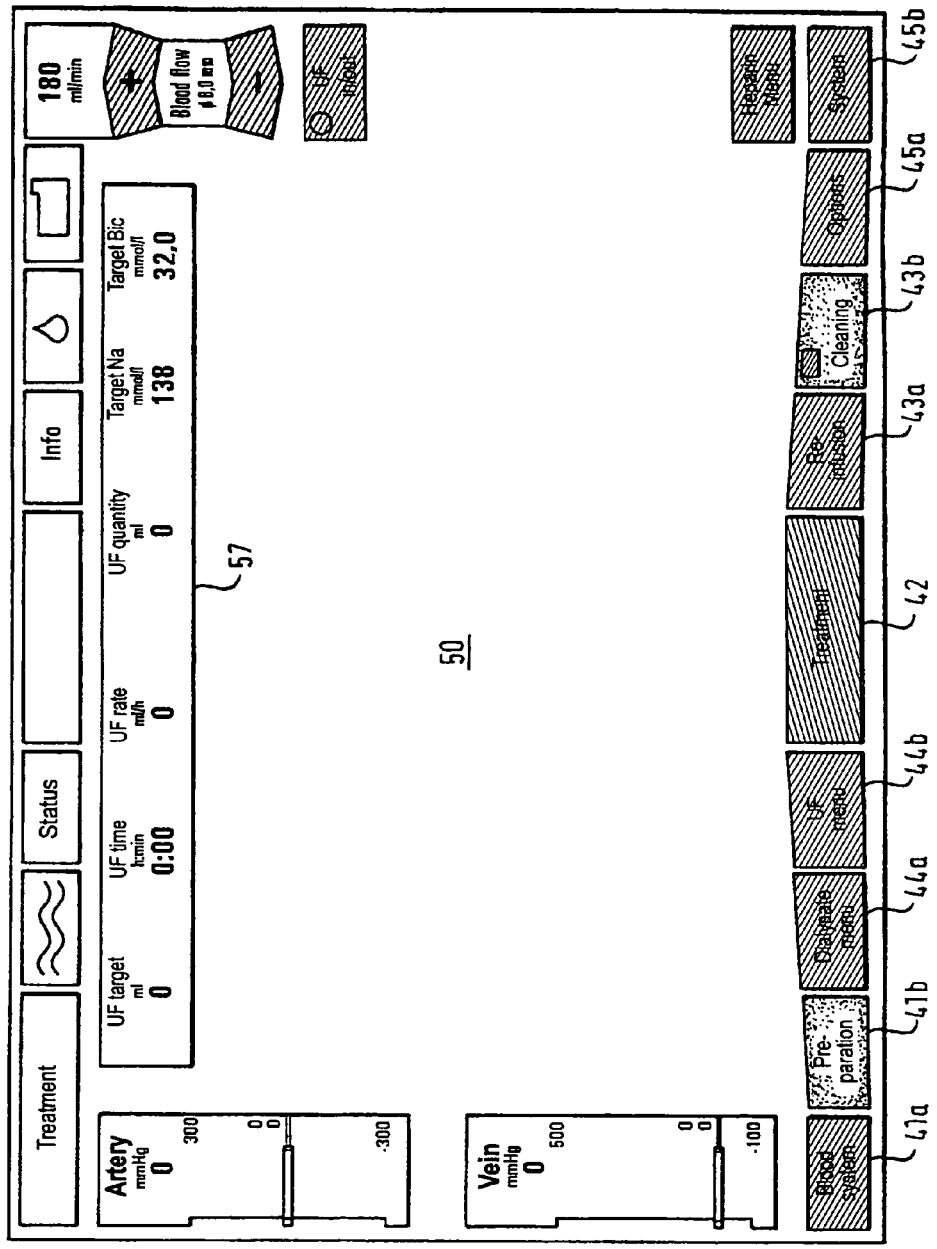
FIG. 4 is a third view of the touch screen of the haemodialysis device with various mode means, wherein the mode means "treatment" is selected.

The operator now connects the blood supply line 5 and the blood return line 7 to a blood vessel in the patient. The blood pump 6 must then be set in operation again using the blood pump activating means 56. As soon as blood is identified in the air and blood detector 9, the blood treatment can begin. For this purpose the air and blood detector 9 has an optical detector which examines the colour of a medium in the blood return line 7 by a suitable choice of wavelength using the transmitted light method. The corresponding signal is received by the control unit 30 which thereby selects the next temporally successive operating mode and communicates this to the display and input unit 32 for the corresponding display. The view shown in FIG. 4 is then displayed on the touch screen 33.

The temporal mode now introduced automatically is the treatment mode, i.e., the actual haemodialysis treatment begins. In the treatment mode the data strip 57 is displayed on the display area 50. Data strip 57 reproduces treatment progress parameters such as the elasped treatment time and the ultrafiltration quantity already removed.

Basic values of the dialysis fluid composition such as the sodium and bicarbonate concentration are also displayed.

Figure 5:
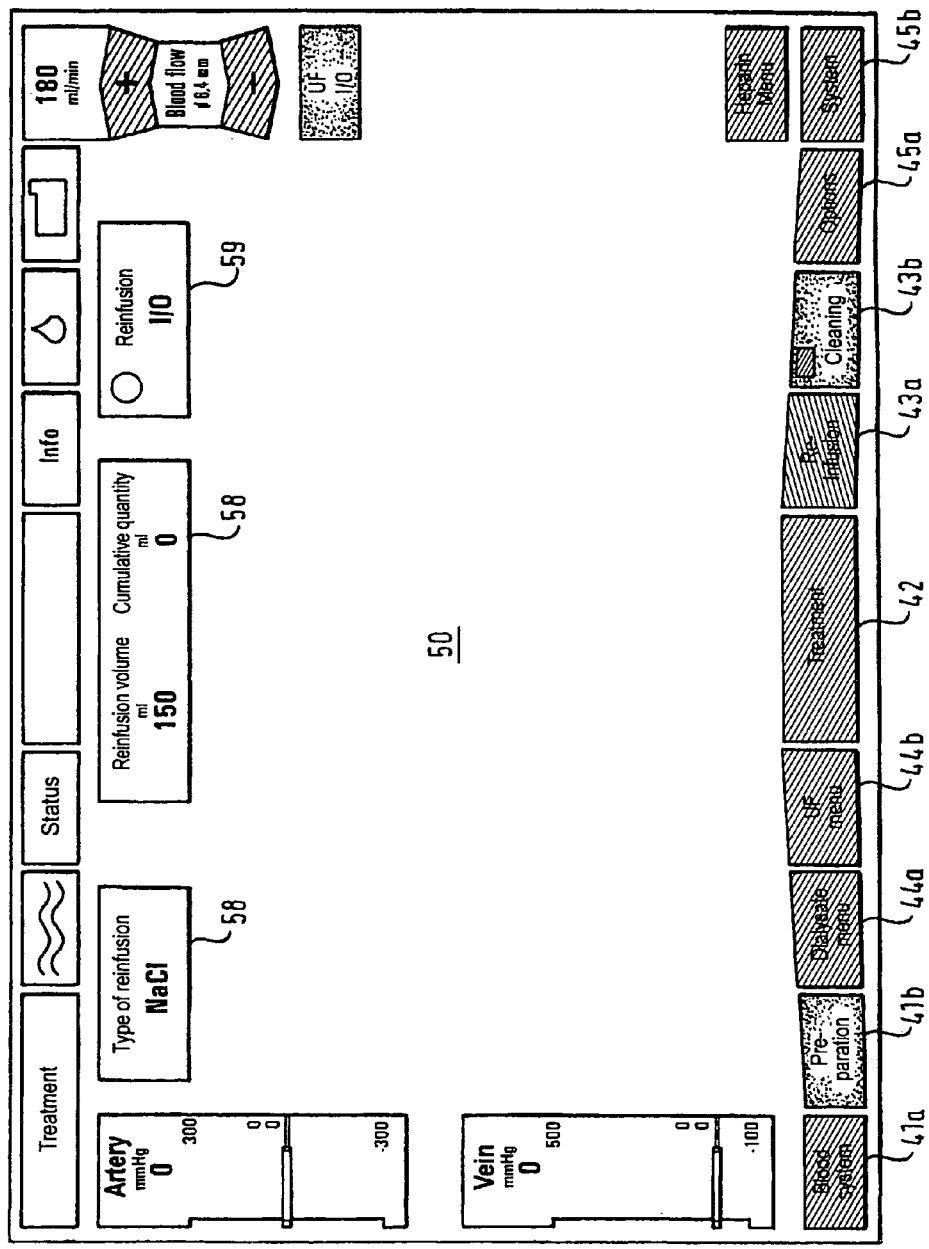
FIG. 5 is a fourth view of the touch screen of the haemodialysis device with various mode means, wherein the mode means "re-infusion" is selected.

If a pre-determined treatment target is achieved, e.g. a total ultrafiltration quantity to be removed, the haemodialysis treatment is stopped by the control unit 30 by stopping the blood pump 6. According to the invention, the temporally successive re-infusion mode is also initiated by the control unit 30. For this purpose the display and input unit 32 is instructed by the control unit 30 to change to the view in accordance with FIG. 5.

The operator now separates the blood supply line 5 from the patient and re-connects the bag containing isotonic sodium chloride solution to this line. In the data strip 58 data on the re-infusion to take place are displayed by analogy with the data strip 55. The re-infusion can be started with the aid of the blood pump activating means 59. The control unit 30 controls the blood pump 6 such that a pre-determined blood hose volume of 150 ml in this example is conveyed in order to return the blood in the extracorporeal circulatory system back to the patient via the blood return line 7. After conveying the pre-determined quantity of fluid, the control unit 30 according to the invention initiates the next temporally successive mode—the purification mode.

Figure 6:
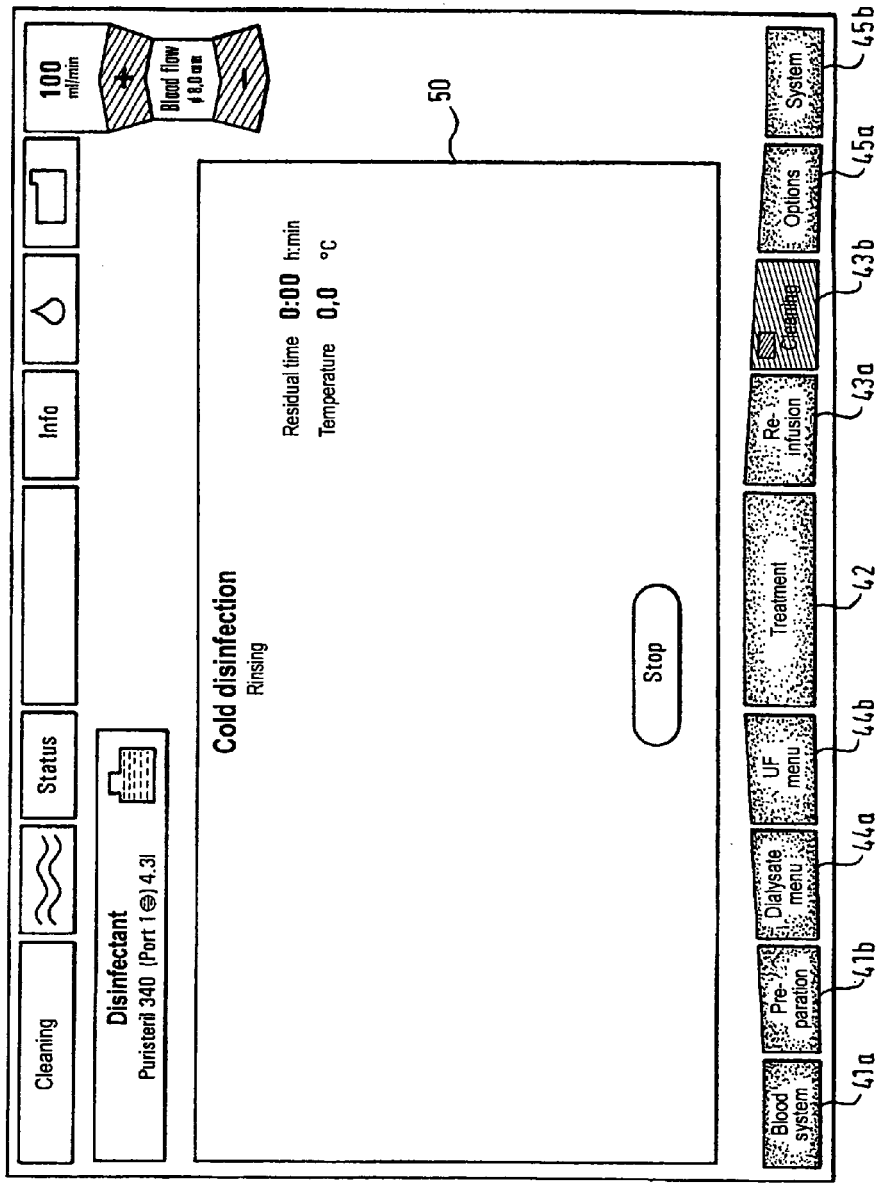
FIG. 6 is a fifth view of the touch screen of the haemodialysis device with various mode means, wherein the mode means "purification" is selected.

In the purification mode the display and input unit 32 displays the view which can be seen in FIG. 6. The patient is now completely separated from the haemodialysis device by the operator before flushing and disinfection steps are initiated. During the purification operating parameters are displayed on the display area 50. The haemodialysis device has thus reached the end of the individual temporal treatment modes for a haemodialysis treatment.

The embodiment of the haemodialysis device according to the invention simplifies the operator management by the automatic selection of the mode means described with the introduction of temporally successive operating modes and thereby helps to avoid incorrect operations. In addition, an arrangement of the mode means corresponding to the time sequence improves the clarity of the touch screen elements. This also applies to the permanent visibility of the individual mode means in all views regardless of the operating mode, which represents a particularly advantageous embodiment. As a result of the automatic selection of subsequent operating modes, the operator is additionally unburdened since fewer inputs are required.

This particularly applies in cases where, in addition to changing the representation on the touch screen at the beginning of a subsequent temporal mode, actuators of the blood treatment device are also automatically set in motion. In the example shown this was the case on transition from the preparation mode to the treatment mode.

In order to increase the clarity it can be provided when controlling the touch screen to vary the appearance of the symbols used for the individual mode means. The mode means 40 in FIGS. 2 to 6 accordingly varies in height with the highest value for the blood treatment means 42. Towards the blood treatment preparation means 41a and 41b and the blood treatment after-preparation means 42a and 42b, the height decreases in order to give these three temporal regions an additional clarity, with the blood treatment means 42 being emphasised.

The mode means 40 can comprise further supplementary mode means 44a, 44b, 45a and 45b not mentioned so far. In the example shown in FIGS. 2 to 6 treatment values differing from the treatment base values can be input using the dialysate mode means 44a and the ultra-filtrate mode means 44b. Manual selection of these mode means is especially suitable during the preparation of a haemodialysis treatment. For this reason these mode means are arranged on the blood treatment preparation side of the mode means 40. However, it is also possible to change the corresponding treatment parameters such as, for example, dialysis liquid flow, ultra-filtration quantity, treatment time etc. manually during a haemodialysis treatment before the end of the treatment by selecting these mode means.

The options mode means 45a is reserved for the extension functions of the haemodialysis equipment which likewise influence the course of a haemodialysis treatment or at least make available further measured data for their monitoring. The system mode means 45b concerns equipment settings such as the loudness of a loudspeaker or the brightness of the display which can be changed at any time and which are not directly related to the blood treatment.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed:

1. A blood treatment unit comprising
    a blood treatment device that is part of an extracorporeal blood circulatory system, said system including a blood line, a blood pump, and a contact sensor associated with the blood pump,
    actuators in at least one of the extracorporeal blood circulatory system and another fluid circulatory system,
    a control unit for controlling the actuators, and
    a display and input unit including a touch screen connected to the control unit,
    the display and input unit including on the touch screen a plurality of mode means selectable to influence operation of a blood treatment, the mode means being configured to display various time modes of the blood treatment to be selectable by an operator via the touch screen, and to be sequentially arranged with respect to one another in order of their occurrence in time during the blood treatment, and including a blood treatment preparation means that includes a blood system mode and a preparation mode, one blood treatment means, and one blood treatment after-preparation means, and
    the control unit being programmed
    (i) to identify the respectively running time mode and to instruct the display and input unit to show the corresponding mode means selected from other mode means, by showing the other mode means in a first type of symbol and the selected mode means in a second type of symbol,
    (ii) to establish an end of at least one of the time modes,
    (iii) to automatically initiate a beginning of a subsequent time mode, and (iv) to communicate the initiation of the time mode to the display and input unit for changing the representation of the selected mode means, with the blood treatment unit being configured such that at the beginning of the blood treatment, the blood treatment device initiates the blood system mode, and (a) if a proper insertion of the blood hose is not detected by the contact sensor, the blood system mode remains active, with the blood system mode being displayed on the control unit, and (b) once a proper insertion of the blood hose is detected by the contact sensor, the control unit initiates the end of the blood system mode and the initiation of the reparation mode, with the preparation mode being displayed on the control unit.

2. The blood treatment unit according to claim 1, wherein the blood treatment means on the touch screen has a larger area than the blood treatment preparation means and the blood treatment after-preparation means.

3. The blood treatment unit according to claim 1, wherein the mode means are represented as a cell at one edge of the touch screen and a remaining area of the touch screen represents at least one of other output means and input means.

4. The blood treatment unit according to claim 1, wherein the touch screen has a display area on which the display and input unit represents at least one of an output means and an input means depending on the time mode.

5. The blood treatment unit according to claim 1, wherein the blood treatment device is a haemodialysis device.

6. The blood treatment unit according to claim 5, wherein the at least one blood after-preparation means includes mode means each for a re-infusion mode and a purification mode.

7. The blood treatment unit according to claim 1, wherein the control unit instructs the display and input unit to represent individual mode means in a third type of symbol according to the running time mode and to deactivate an input function associated therewith.

8. The blood treatment unit according to claim 1, wherein the display and input unit displays the mode means in all of the time modes at a same point of the touch screen.

9. The blood treatment unit according to claim 1, further comprising a plurality of sensors, and wherein the control unit evaluates measured values of the sensors in order to determine the end of a time mode.

10. The blood treatment unit according to claim 9, wherein the sensors include at least one of a blood detector and an air detector in the extracorporeal circulatory system.

11. The blood treatment unit according to claim 9, wherein the sensors include a detector to determine the presence of correctly mounted components of the extracorporeal circulatory system.

12. The blood treatment unit according to claim 1, wherein the control unit determines a quantity of fluid conveyed by a controlled pump at a certain time in order to use the quantity value to determine the end of a time mode.

13. A blood treatment unit comprising;
a blood treatment device that is part of an extracorporeal blood circulatory system, said system including a blood line, a blood pump, and a contact sensor associated with the blood pump;
a plurality of actuators in at least one of the extracorporeal blood circulatory system and another fluid circulatory system;
a control unit to control the actuators; and
a display and input unit having a touch screen for input, the display and input unit being in communication with the control unit, the display and input unit including a plurality of mode touch screen areas that display modes of the blood treatment on the touch screen, the mode touch screen areas being selectable by an operator and being arranged sequentially on the touch screen in order of their occurrence in time during the blood treatment, and including at least one of the mode touch screen areas for each of a blood treatment preparation mode that includes a blood system mode and a preparation mode, a blood treatment mode, and a blood treatment post-preparation mode, and the control unit being programmed
(i) to identify which of the modes is operating and to instruct the display and input unit to display on the touch screen the corresponding mode touch screen area, the display and input unit showing the operating mode by a first type of symbol and showing non-operating modes by a second type of symbol,
(ii) to establish an end of at least one of the modes,
(iii) to automatically initiate a beginning of a subsequent mode, and
(iv) to communicate the initiation of the subsequent mode to the display and input unit for changing the representation of the operating mode, with the blood treatment unit being configured such that at the beginning of the blood treatment, the blood treatment device initiates the blood system mode, and (a) if a proper insertion of the blood hose is not detected by the contact sensor, the blood system mode remains active, with the blood system mode being displayed on the control unit, and (b) once a proper insertion of the blood hose is detected by the contact sensor, the control unit initiates the end of the blood system mode and the in of the preparation mode, with the preparation mode displayed on the control unit.

14. The blood treatment unit according to claim 13, wherein the mode touch screen areas are configured as a cell at one edge of the touch screen, and a remaining area of the touch screen includes at least one of output touch screen areas and input touch screen areas associated with the blood treatment.

15. The blood treatment unit according to claim 13, wherein the touch screen area for the blood treatment preparation mode includes a touch screen area for each of the blood system mode and the preparation mode, and the touch screen area for the blood post-preparation mode includes a touch screen area for each of a re-infusion mode and a purification mode.

16. A blood treatment unit comprising
a blood treatment device that is part of an extracorporeal blood circulatory system, said system including a blood line, a blood pump, and a contact sensor associated with the blood pump,
actuators in at least one of the extracorporeal blood circulatory system and another fluid circulatory system,
a control unit for controlling the actuators, and
a display and input unit including a touch screen connected to the control unit,
the display and input unit including on the touch screen a plurality of mode means selectable to influence operation of a blood treatment, the mode means being configured to display various time modes of the blood treatment to be selectable by an operator via the touch screen, and to be sequentially arranged with respect to one another in order of their occurrence in time during the blood treatment, and including at least one blood treatment preparation means that includes a blood system mode and a preparation mode, one blood treatment means, and one blood treatment after-preparation means, the individual mode means being permanently visible in all views, and the control unit being programmed
(i) to identify the respectively running time mode and to instruct the display and input unit to show the corresponding mode means selected from other mode means, by showing the other mode means in a first type of symbol and the selected mode means in a second type of symbol,
(ii) to establish an end of at least one of the time modes,
(iii) to automatically initiate a beginning of a subsequent time mode, and
(iv) to communicate the initiation of the time mode to the display and input unit for changing the representation of the selected mode means, with the blood treatment unit being configured such that at the beginning of the blood treatment, the blood treatment device initiates the blood system mode, and (a) if a proper insertion of the blood hose is not detected by the contact sensor, the blood system mode remains active, with the blood system mode being displayed on the control unit, and (b) once a proper insertion of the blood hose is detected by the contact sensor, the control unit initiates the end of the blood system mode and the initiation of the preparation mode, with the preparation mode being displayed on the control unit.

17. A blood treatment unit comprising:

a blood treatment device that is part of an extracorporeal blood circulatory system, said system including a blood line, a blood pump, and a contact sensor associated with the blood pump;

a plurality of actuators in at least one of the extracorporeal blood circulatory system and another fluid circulatory system;

a control unit to control the actuators; and a display and input unit having a touch screen for input, the display and input unit being in communication with the control unit, the display and input unit including a plurality of mode touch screen areas that display modes of the blood treatment on the touch screen, the mode touch screen areas being selectable by an operator and being arranged sequentially on the touch screen in order of their occurrence in time during the blood treatment, and including at least one of the mode touch screen areas for each of a blood treatment preparation mode that includes a blood system mode and a preparation mode, a blood treatment mode, and blood treatment post-preparation mode, the individual mode touch screen areas being permanently visible in all views of the mode touch screen areas regardless of which of the blood treatment modes is in operation, and the control unit being programmed
(i) to identify which of the modes is operating and to instruct the display and input unit to display on the touch screen the corresponding mode touch screen area, the display and input unit showing the operating mode by a first type of symbol and showing non-operating modes by a second type of symbol,
(ii) to establish an and of at least one of the modes,
(iii) to automatically initiate a beginning of a subsequent mode, and
(iv) to communicate the initiation of the subsequent mode to the display and input unit for changing the representation of the operating mode, with the blood treatment unit being configured such that at the beginning of the blood treatment, the blood treatment device initiates the blood system mode, and (a) if proper insertion of the blood hose is not detected by the contact sensor, the blood system mode remains active, with the blood system mode being displayed on the control unit, and (b) once a proper insertion of the blood hose is detected by the contact sensor, the control unit initiates the end of the blood system mode and the initiation of the preparation mode, with the preparation mode being displayed on the control unit.

* * * * *